(12) United States Patent  (10) Patent No.: US 6,585,711 B1
Lohrasbi  (45) Date of Patent: Jul. 1, 2003

(54) NURSING DRIBBLE PAD

(76) Inventor: Marilyn J. Lohrasbi, 589 Midland Dr., O'Fallon, MO (US) 63366

( * ) Notice: Subject to any disclaimer, the term of this patent is extended or adjusted under 35 U.S.C. 154(b) by 0 days.

(21) Appl. No.: 09/566,414

(22) Filed: May 8, 2000

Related U.S. Application Data

(60) Provisional application No. 60/133,795, filed on May 12, 1999.

(51) Int. Cl.⁷ .................................................. A61F 13/15
(52) U.S. Cl. .................................................. 604/385.07
(58) Field of Search ........................ 604/385.01, 385.03, 604/385.05, 385.07, 358, 386–390, 346, 355; 2/463, 53; 450/36–37; 222/108; 128/890

(56) References Cited

U.S. PATENT DOCUMENTS

| | | |
|---|---|---|
| 1,449,335 A | 3/1923 | Latham |
| 1,669,061 A | 5/1928 | Meltzer |
| 2,154,772 A | 4/1939 | Rathemacher |
| 2,706,571 A | 4/1955 | Ryan |
| 4,437,583 A | 3/1984 | O'Connor |
| 5,722,966 A | 3/1998 | Christon et al. |
| 5,858,014 A * | 1/1999 | Kepes et al. ................. 604/387 |

* cited by examiner

*Primary Examiner*—Weilun Lo
*Assistant Examiner*—C Anderson
(74) *Attorney, Agent, or Firm*—Polster, Lieder, Woodruff & Lucchesi, L.C

(57) ABSTRACT

The present invention provides a nursing dribble pad which is applied by adhesive to either the mother's breast or the top of a nursing bottle so as to absorb any dribbled liquid on the region around the mouth of the infant when nursing. The dribble pad is soft and rapidly absorbs substantially all liquid which dribbles from the infant's mouth. The dribble pad has a facing layer, an absorbent layer and a liquid impermeable layer.

9 Claims, 1 Drawing Sheet

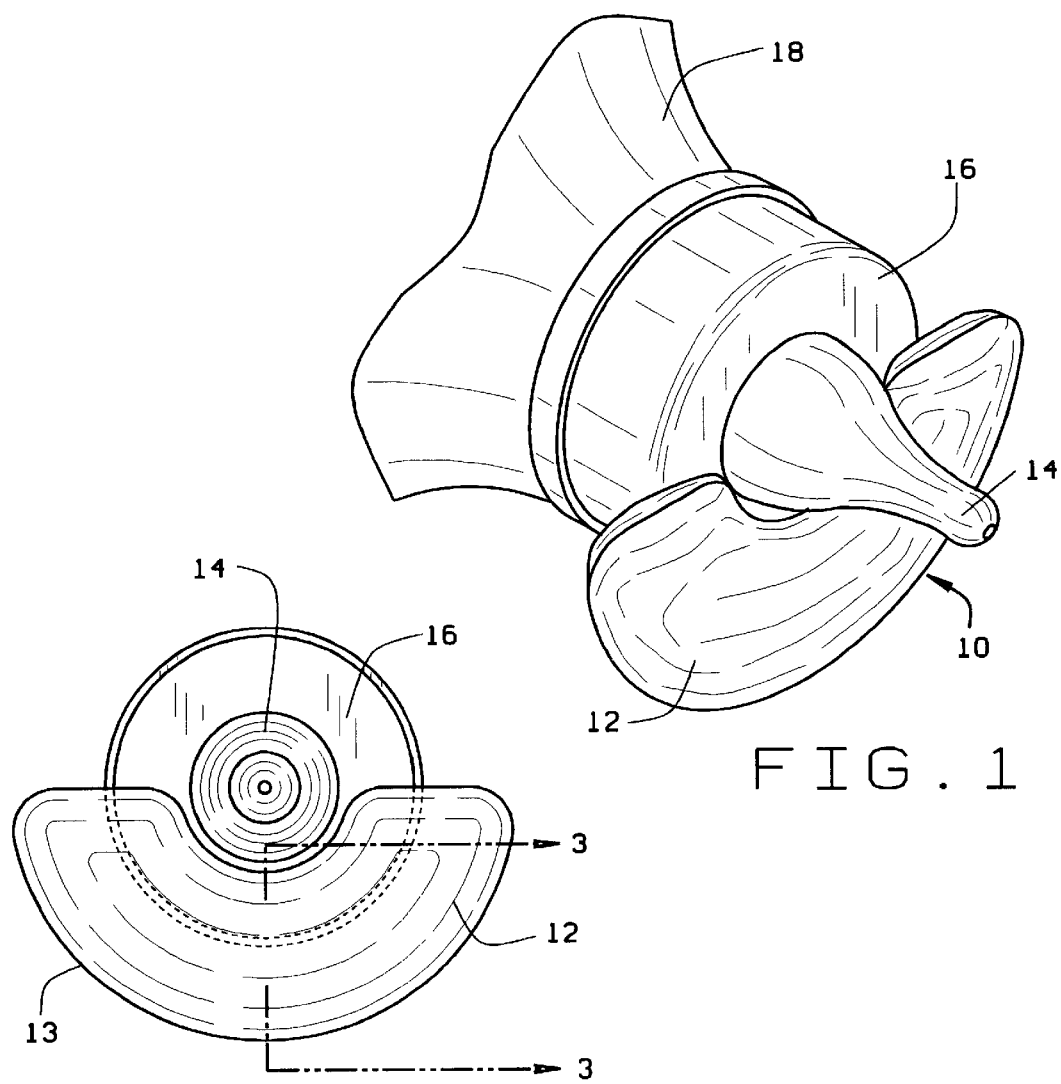
FIG. 1
FIG. 2
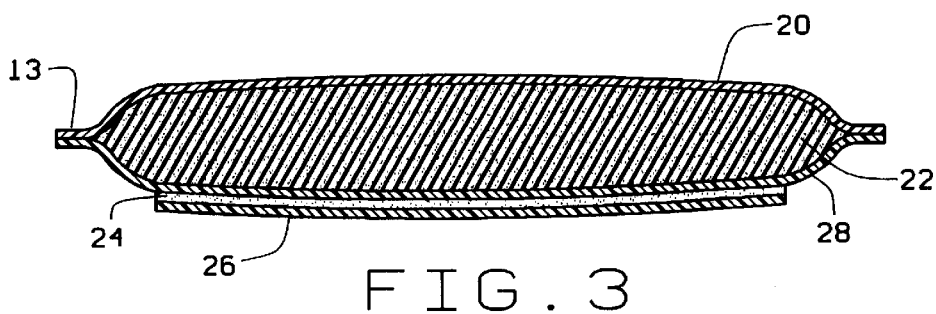
FIG. 3

NURSING DRIBBLE PAD

CROSS-REFERENCE TO RELATED APPLICATIONS

This application is based upon copending provisional application Ser. No. 60/133,795, filed May 12, 1999.

STATEMENT REGARDING FEDERALLY SPONSORED RESEARCH OR DEVELOPMENT

Not applicable.

FIELD OF INVENTION

The present invention relates to a nursing dribble pad utilized with a nursing bottle or when nursing from the mother's breast. The dribble pad is placed around the neck of the bottle against the nipple and likewise around the nipple of the mother's breast. The dribble pad is a half toroid (half a doughnut) in shape and the pad is placed on the side of the nipple where the infant's chin rests.

BACKGROUND OF THE INVENTION

When an infant nurses some of the formula from a bottle or mother's milk dribbles out of the side of the infant's mouth. Because the skin of an infant is tender, the dribbled liquid sometimes causes skin irritation. The irritation may manifest itself in redness of the skin, a rash or the like. The mother will periodically wipe the mouth of the infant, but in the meantime, skin irritation may appear.

The prior art has provided bottle protectors such as that of U.S. Pat. No. 1,449,335 which provides a strip of blotter attached about the circumference of the bottle so that if the contents of the bottle runs down the side of the bottle after use, the blotter absorbs the dribble.

U.S. Pat. No. 2,706,571 to Ryan provides a bottle muff to keep the bottle from breaking. The muff is removed when the bottle is used.

U.S. Pat. No. 4,437,583 to O'Connor provides a dribble ring for a bottle which ring contains an absorbent foam which is impregnated with a neutralizing agent to chemically neutralize any of the bottle contents which leak out onto the dribble ring. The ring protects the hands of the user of the bottle from exposure to the contents of the bottle when there is any leakage around the bottle stopper. The chemical neutralizer may contain an indicator so as to alert the user of seepage of the contents of the bottle.

None of the prior art addresses the problem solved by the invention of applicant The present invention provides a nursing dribble pad which absorbs any liquid dribbled from the mouth of an infant when nursing and prevents skin irritation around the mouth of the infant.

SUMMARY OF THE INVENTION

The present invention provides a nursing dribble pad which is applied by adhesive to either the mother's breast or the top of a nursing bottle so as to absorb any dribbled liquid on the region around the mouth of the infant when nursing. The dribble pad is soft and rapidly absorbs substantially all liquid which dribbles from the infant's mouth.

The dribble pad has a half toroid shape (i.e., a half doughnut shape) and is comprised of a facing layer of liquid permeable material; an absorbent layer juxtaposed beneath the facing layer; a liquid impermeable layer juxtaposed beneath the absorbent layer; and an adhesive portion applied to the exterior of the liquid impermeable layer to allow adherence to the bottle top or the mother's breast so as to hold the dribble pad in place. Each of the facing layer and the liquid impermeable layer extend beyond the periphery of the absorbent layer and the extended portions of the facing layer and the liquid impermeable layer are joined together so as to encase the absorbent layer.

The dribble pad has a substantially semi circular shape with a cutout of semi circular shape in the center of the flat side to form half a toroid or half a doughnut in shape. The half doughnut shape fits halfway around the nipple of either the mother or a bottle. By snuggly fitting the dribble pad against the nipple, substantially none of the nursing liquid which dribbles from the infant's mouth remains on the facial skin of the infant. It is expedient to place the dribble pad on the lower portion surrounding the nipple because the dribbled liquid tends to migrate downward toward the chin of the infant. If desired, two of the dribble pads could be used simultaneously to protect the entire region surrounding the nipple.

The dribble pad is comprised of a facing layer of soft liquid permeable material such as cotton fabric, a nonwoven fabric, apertured film, or the like. Adjacent the facing layer is an absorbent layer of adequate thickness so as to absorb the liquid dribble and retain it. The absorbent layer is comprised of absorbent fibers which may be wood pulp fibers, other natural fibers or synthetic fibers or an absorbent foam. The fibers preferably are hydrophilic so as to readily attract and absorb liquid. A substance, such as a superabsorbent material may be added to the foam or fibrous material in the absorbent pad so as to enhance the capacity of absorption by the layer. Typical superabsorbent materials include polysodium acrylate or the like.

On the opposite side of the absorbent layer from the facing layer, there is a liquid impermeable layer comprised of liquid impermeable film such as polyethylene film, polypropylene film or the like. The liquid impermeable layer prevents leakage of absorbed liquid from the absorbent layer and keeps the surface around the nipple substantially dry. The facing layer and the liquid impermeable layer extend about the periphery of the absorbent layer in such a manner as to allow the two outside layers to be sealed one to the other so as to encase the absorbent layer.

Adhesive is applied to at least a portion of the outside liquid impermeable layer to allow the dribble pad to be held in place on the outer surface surrounding the nipple of the nursing bottle or the skin surrounding the nipple of the nursing mother. Any adhesive suitable for adherence to human skin may be used. It is preferable to cover the adhesive application with a releasable strip to protect the adhesive until the time for use whereupon the protective strip is removed and the dribble pad is adhered in place for use.

BRIEF DESCRIPTION OF THE DRAWINGS

FIG. 1 is a perspective view of one embodiment of the invention;

FIG. 2 is a top plan view of another embodiment of the invention; and

FIG. 3 is a section elevational view taken along line 3—3 of FIG. 2.

DETAILED DESCRIPTION OF THE INVENTION

FIG. 1 depicts the upper portion of a nursing bottle with a dribble pad attached 10. The dribble pad 12 is adhesively attached to the flat portion of the nursing bottle cap 16 partially surrounding the nipple 14 of the bottle 18.

FIG. 2 is a top plan view showing the relationship of the dribble pad 12 to the nipple 14 of a typical nursing bottle cap 16.

FIG. 3 is a section view taken along line 3—3 of FIG. 2 where the construction of the dribble pad 12 becomes apparent. The dribble pad 12 has a moisture permeable layer 20 on the top of the pad 12 which permits the dribble from nursing to penetrate to an absorbent layer 22 which absorbs and holds any dribble from the infant's mouth. The absorbent layer 22 is formed from absorbent material for example, wood pulp fiber, synthetic hydrophilic fibers, absorbent foam, other natural fibers, superabsorbent material, mixtures thereof and the like.

On the opposite side of the absorbent layer 22, is a liquid impermeable layer 28 to prevent the nursing dribble from leaking from the absorbent portion 22 of the pad 12. The liquid impermeable layer 28 is a suitable thin film, for example, polyethylene, polypropylene or the like. The permeable layer 20 and the impermeable layer 28 extend beyond the periphery of the absorbent pad 22, and are joined at the edge 13 of the pad 12 by heat sealing, glue or other suitable means for sealing the edge 13. Thus the absorbent layer 22 is encased within the envelope created by the sealing of the edges 13 of the facing layer 20 and the liquid impermeable layer 28.

A portion of the impermeable film 28 is treated with an adhesive 24 suitable for attaching the dribble pad 12 to the nursing bottle 18 or the mother's breast (not shown) just below the nipple 14 to hold the pad 12 securely while the infant nurses. The adhesive layer 24 preferably is covered with a release layer 26 which is easily removed at the time of use of the pad 12. Any suitable adhesive 24 may be used which allows the pad 12 to be affixed to the mother's breast or the surface of a bottle cap 16.

What is claimed is:

1. A dribble pad for protecting the lower area around the mouth of a baby suckling a nipple, said nipple having an area surrounding it from which the nipple projects, said pad lying in a flat plane and being a half-toroid in shape, with an opening taking the form of a notch in an upper margin of said half-toroid pad, said nipple extendable into said notch having a shape complimentary to the area immediately surrounding the nipple and said pad being positioned immediately below the nipple when the baby is suckling, said dribble pad comprising:

(a) an outwardly facing layer of liquid permeable material;
    (b) an absorbent layer juxtaposed beneath the facing layer;
    (c) a liquid impermeable layer juxtaposed beneath the absorbent layer and lying against the area immediately adjacent said nipple, and (d) an adhesive portion applied to the exterior of the liquid impermeable layer, adapted gently to adhere to an area around said nipple, each of the facing layer and the liquid impermeable layer having portions extending beyond the periphery of the absorbent layer, the extended portions of the facing layer and the liquid impermeable layer being joined together to encase the absorbent layer.

2. The dribble pad of claim 1 wherein the facing layer is cotton fabric, a non-woven fabric, or an apertured film.

3. The dribble pad of claim 1 wherein the absorbent layer is absorbent foam, wood pulp fibers, or synthetic hydrophilic fibers, superabsorbent material or mixtures thereof.

4. The dribble pad of claim 3 wherein the absorbent layer is a mixture of wood pulp fibers and superabsorbent material.

5. The dribble pad of claim 1 wherein the liquid impermeable layer is a polyethylene film.

6. The dribble pad of claim 1 wherein the adhesive portion has a removable protective strip cover the adhesive until time for use of the dribble pad.

7. The dribble pad of claim 1 wherein the facing layer is a non-woven fabric, the absorbent layer is wood pulp fibers containing superabsorbent material and the liquid impermeable layer is a polyethylene film.

8. The dribble pad of claim 1 wherein the extended portions of the outwardly extending facing layer and liquid impermeable layer are bonded to each other by means of heat sealing.

9. The dribble pad of claim 1 wherein the extended portions of the facing layer and liquid impermeable layer are adhered to each other by means of adhesive.

\* \* \* \* \*